United States Patent [19]

Madray, Jr.

[11] Patent Number: 5,076,791

[45] Date of Patent: Dec. 31, 1991

[54] PROFESSIONAL HOME METHOD FOR BLEACHING TEETH

[76] Inventor: George Madray, Jr., #4 Carteret Rd., Brunswick, Ga. 31520

[21] Appl. No.: 602,076

[22] Filed: Oct. 22, 1990

[51] Int. Cl.$^5$ .......................... A61C 5/00; A61C 15/00
[52] U.S. Cl. ..................................... 433/215; 433/216
[58] Field of Search .................. 433/80, 136, 215, 216, 433/217.1, 229

[56] References Cited

U.S. PATENT DOCUMENTS

| | | | |
|---|---|---|---|
| 803,475 | 10/1905 | Dennis | 433/80 |
| 4,044,762 | 8/1977 | Jacobs | 128/136 |
| 4,968,251 | 11/1990 | Darnell | 433/216 |
| 4,983,381 | 1/1991 | Zaragoza | 424/53 |
| 4,990,089 | 2/1991 | Munro | 433/215 |
| 5,032,178 | 7/1991 | Cornell | 106/35 |

FOREIGN PATENT DOCUMENTS 0286766 10/1988 European Pat. Off. ............ 433/216

Primary Examiner—John J. Wilson
Assistant Examiner—Cindy A. Cherichetti

[57] ABSTRACT

An improved method for bleaching teeth using a preformed stock tray of a thermoplastic material with a low-heat melt-index, and a peroxide gel. The tray is custom fitted at home by the wearer, instead of having to go to a dentist. It is placed in boiling water a few seconds to soften, and is adapted snugly over the teeth in one arch. An oxidizing gel of an over-the-counter oral antiseptic is placed inside the tray, which in turn is placed over the teeth. After a period of time the gel is replenished again. This is done several times throughout the day, and continued for 2-3 weeks. The end result being whiter teeth and a new smile.

9 Claims, No Drawings

PROFESSIONAL HOME METHOD FOR BLEACHING TEETH

FIELD OF THE INVENTION

This invention relates to a process of bleaching (or whitening) the dentition and more particularly is related to a person being able to whiten the teeth at home, with a mouth tray, without requiring the assistance of a dentist.

BACKGROUND OF THE INVENTION

Heretofore, people with stained teeth from pathologic and non-pathologic reasons, have had to go to a dentist for the cosmetic lightening of the dentition. One method is known as power bleaching. It involves caustic solutions of hydrogen peroxide (35%) and phosphoric acid (35%) with heat and or light. This requires 4-12 visits to a dental office, where diligent protection of the gums and oral mucosa have to be done. This requires approximately 1-hour per visit, and a fee assessed accordingly. These caustic solutions produce rough enamel and not uncommonly, dental sensitivity.

More recently there has been the advent of matrix bleaching. This still involves going to a dentist for the fabrication of a matrix. It is a plastic tray that fits over the teeth, for the purpose of containing a peroxide gel with a hydrogen peroxide content of from about 1.5%-6%, or its equivalent. The patient has to have impressions made of the teeth, casts fabricated, and a plastic sheet melted and vacuum formed to the casts, which then has to be trimmed and fitted. The fitting when done properly generally involves selective grinding, (occlusal equilibration) on the now plastic matrix or tray in order for the anterior teeth to occlude simultaneously along with the posterior teeth against the tray. This is important as well as involved. If, when a person swallows, the posterior teeth occlude on this plastic matrix (tray) without the anterior teeth occluding, then the TMJ (temperomandibular joint) is tweeked, or twisted. This leads to a complete syndrome of problems—from headaches, neck aches, muscle spasms and chronic jaw joint pain to mental neurosis. This of course, takes time.

Patients can't seem to get their teeth too white! For this reason, they are wearing their trays much longer than the dentist ever intended. Those dentist who did not equilibrate (selectively grind) the tray (matrix) and did not expect the patient to wear their tray for so long, are creating potential problems later, as well as real problems currently. It is only at this time that we dentists are discovering these newly created problems and concerns. A solution is needed to this, due to the very devastating nature of a full blown TMJ syndrome; and to the potential seeding of that syndrome. Many dentist do not realize the insidious beginnings of the problems that they are treating in this new and burgeoning field of cosmetic bleaching. Perhaps one of the reasons why this invention hasn't been thought of before.

The only other method for whitening teeth, the swab-on method, can be tracked back to 1907. It involves swabbing hydrogen peroxide on the teeth. Reference is made to a book by Gardner D. Hiscox, Henleys Twentieth Century Formulas, Recipes and Processes, Norman Henley Pub. Co., N.Y. 1927 p. 705. This method has been brought back with great popularity and promoted on television and in pharmacies. It is not very effective, since the effectiveness of bleaching is determined by the contact time of the bleach on the teeth, according to research by the Clinical Research Associates in Provo, Utah. This is stated in the CRA Newsletter, Vol. 13, Issue 12—Dec. 1989, p. 1, Provo, Utah. There is also safety concerns of long term exposure of hydrogen peroxide, which is necessary with this method, due to its ineffectiveness.

Since my invention was recognized in the professional publication— Dental Products Report, November 1989, several competitors have found it novel and worthy of infringement by manufacturing products very similar, in order to copy the process thereby accomplishing its objectives, and advantages.

OBJECTS AND ADVANTAGES

Accordingly, a number of objects and advantages are present with this new method of bleaching teeth. The cost is greatly reduced, because there is no need to go to a dentist for the manufacture of the tray—it can be fabricated from an injection molded thermoplastic tray which cost only pennies to manufacture. The tray used in the process is much safer in that it does not "tweek" the TMJ, and because of its balanced occlusion is more comfortable to wear.

Other objectives and advantages are the speed and safety in which the teeth are bleached—over the power bleaching method. The process takes 2-3 weeks compared to the 4-12 weeks for power bleaching. There are no caustic solutions used which can burn the patient or cause untoward dental sensitivity, or rough enamel.

The novel process provides an alternative method in and of itself, with a tray that can be repaired at home and is generally more comfortable and more durable than the tray used in matrix bleaching, due to its different composition, making it more acceptable. Additionally, the process is more convenient to do at home and saves the time required for trips to a dentist. Also, there are advantages over the swab-on method. Results are achieved in 2-3 weeks -vs- months on end. Safety concerns of long-term exposure to a peroxide gel is reduced. Lastly, the method of the invention only takes about 5 seconds to apply, compared with about 5 minutes with the swab-on method.

Finally, due to the existing psychological need for a better appearance and a brighter smile, with the above mentioned advantages, its marketability is greater. The market size may be as great as the users of toothpaste. The market trend is increasing and with the more marketability, marketers are easier to locate and the masses can now be reached, with little regard to social-economic status.

Further objects and advantages of the invention will become apparent from a consideration of the description.

DESCRIPTION OF INVENTION

This professional home method of bleaching teeth involves placing a tray, which contains a bleaching gel, over the teeth, to whiten them. The method is known as the professional method because it is done the same way dental professionals do it—namely, with a tray.

The tray can be an athletic mouthguard. This mouthguard is generally used for protection in contact sporting events like boxing or football. It is a thermoplastic material with a low melt index, meaning that it can be heated in boiling water to the point of softening, and then can be placed around the upper teeth and formed snugly with the fingers, lips, tongue and lower teeth, to custom fit snugly, encompassing the teeth on the upper arch. And of course, vice versa for the lower teeth. The tray can be made of an ethyl vinyl-acetate. By restricting the amount of vinyl-acetate the tray can be made thinner for more comfort and esthetics, rather than for protection, making it more conducive to bleaching.

During the fitting of an upper tray, the lower teeth are gently closed into the tray without biting through it. After the tray cools, it hardens. This enables all the lower teeth to be able to touch the tray at the same time, when a person occludes (e.g. during swallowing)—This will give balanced occlusal harmony improving the current motus operando of vacuum forming, without selective grinding, that currently goes on in dental offices.

The bleaching gel contains active oxygen, which comes from say hydrogen peroxide—a hydrogen peroxide from say 1.5% to less than 6%, or it's equivalent. (This amount has been approved by the FDA for short term treatment as an oral antiseptic. It's side effect, is whitening teeth. The process is much safer than the current home, swab-on method used once or twice a day for 2-3 months. This is because hydrogen peroxide with long term use has been shown by the FDA to cause black hairy tongue, oral inflammation, and tooth decalcification).

The gel is placed into the tray, and the tray is placed over the teeth, of say the upper arch. It is worn from 15 minutes to several hours in a 24 hour period. It may be 1 session for 15 minutes, 1-3 sessions per day; or 1 session for 8 hours (if the person were to sleep with it)—it would all depend upon the active oxygen used, its activity, effectiveness or potential problem development. After 2-3 weeks teeth which have been yellowed from aging for example, are whitened and brightened dramatically.

SUMMARY, RAMIFICATIONS, AND SCOPE OF INVENTION

The process of the invention is ecomonical, convienient, comfortable, safer, more effective and more reliable than present methods.

While the above description contains specifications, these should not be construed as limitations on the scope of the invention, but rather as an exemplification thereof, variations are possible. For example, a thin tray with a grid or etchings on the inside can be added to act as a reservoir to hold additional gel, of any viscosity, which can be urea peroxide, sodium perborate or any combination of any oxidizing or reducing substance.

What is claimed is:

1. A process of bleaching teeth comprising the steps of:
   (a) heating a thermoplastic material which is substantially in the shape of a horseshoe with a U-shaped channel for receiving the teeth in a dental arch, to a temperature in excess of normal human body temperature, to the point of being pliable,
   (b) adapting said thermoplastic material to said teeth with the forefingers and thumbs, lips and tongue, and the teeth in the opposite arch to snugly encompass said teeth so that it is in juxtaposition with said teeth, and that when cooled to the normal human body temperature is resilient and shape retaining whereby a tray is formed, and
   (c) placing a bleaching agent within the confines of said tray and placing said tray over said teeth whereby said agent is held in contact with said teeth.

2. The process as set forth in claim 1 wherein the adapting of said thermoplastic material is performed by occluding the teeth in the opposite arch from said teeth to be bleached, into said material while said material is in its pliable stage where by a balanced occlusion is achieved.

3. The process of claim 1 wherein said thermoplastic material has its tooth contacting surface etched, pimpled or has a grid pattern, giving said material a greater surface area wherein to act as a reservoir whereby additional said bleaching agent can be held in contact with said teeth.

4. The process of claim 1 wherein said thermoplastic material is ethyl vinyl acetate whereby esthetics and comfort is obtained for the person during bleaching.

5. The process of claim 1 wherein said thermoplastic material is immersed in water which has been brought to a boil to make the same pliable for adaptation to said teeth enabling a direct impression to be made of said teeth whereby the need of a dentist or professional to make an impression and subsequent model of said teeth and pressure or vacuum forming a thermoplastic material to said teeth in a laboratory, is totally eliminated.

6. The process of claim 1 wherein said thermoplastic material is inherently resilient to keep from forming a substantially liquid tight seal to said teeth so that saliva can contact and activate said bleaching agent and can allow for ingress and egress of oxygen to the internal surface of said material whereby quicker bleaching of said teeth and less irritation of the gums, can be achieved.

7. The process of claim 1 wherein said bleaching agent is any oxidizing agent in an aqueous or non aqueous base thickened to any viscosity.

8. The process of claim 1 wherein said bleaching agent is any reducing agent in an aqueous or non aqueous base thickened to any viscosity.

9. The process of claim 1 further comprising the steps of periodically removing said tray, adding additional bleaching agent, and replacing said tray containing said additional bleaching agent around said teeth to be bleached.

* * * * *

(12) EX PARTE REEXAMINATION CERTIFICATE (9089th)
United States Patent
Madray, Jr.

(10) Number: US 5,076,791 C1
(45) Certificate Issued: Jun. 26, 2012

(54) PROFESSIONAL HOME METHOD FOR BLEACHING TEETH

(76) Inventor: George Madray, Jr., Brunswick, GA (US)

Reexamination Request:
No. 90/005,292, Mar. 10, 1999

Reexamination Certificate for:
Patent No.: 5,076,791
Issued: Dec. 31, 1991
Appl. No.: 07/602,076
Filed: Oct. 22, 1990

(51) Int. Cl.
*A61C 5/00* (2006.01)
*A61C 15/00* (2006.01)

(52) U.S. Cl. .................................. 433/215; 433/216
(58) Field of Classification Search .............. 433/80, 433/136, 215, 216, 217.1, 229
See application file for complete search history.

(56) References Cited

To view the complete listing of prior art documents cited during the proceeding for Reexamination Control Number 90/005,292, please refer to the USPTO's public Patent Application Information Retrieval (PAIR) system under the Display References tab.

*Primary Examiner* — Andres Kashnikow

(57) ABSTRACT

An improved method for bleaching teeth using a preformed stock tray of a thermoplastic material with a low-heat melt-index, and a peroxide gel. The tray is custom fitted at home by the wearer, instead of having to go to a dentist. It is placed in boiling water a few seconds to soften, and is adapted snugly over the teeth in one arch. An oxidizing gel of an over-the-counter oral antiseptic is placed inside the tray, which in turn is placed over the teeth. After a period of time the gel is replenished again. This is done several times throughout the day, and continued for 2-3 weeks. The end result being whiter teeth and a new smile.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-9 are cancelled.

* * * * *